United States Patent [19]
Fischer et al.

[11] Patent Number: 6,103,939
[45] Date of Patent: Aug. 15, 2000

[54] PROCESS FOR THE PREPARATION OF 1,4-BUTANEDIOL MONOETHERS

[75] Inventors: Rolf Fischer, Heidelberg; Rolf Pinkos, Bad Dürkheim; Martin Schäfer, Ludwigshafen; Arthur Höhn, Kirchheim; Peter Schwab, Bad Dürkheim, all of Germany

[73] Assignee: BASF Aktiengesellschaft, Ludwigshafen, Germany

[21] Appl. No.: 09/426,957

[22] Filed: Oct. 26, 1999

Related U.S. Application Data

[62] Division of application No. 09/180,482, Nov. 12, 1998.
[51] Int. Cl.[7] .............................. C07C 43/00; C07C 41/00
[52] U.S. Cl. .......................... 568/675; 568/673; 568/687; 568/693; 568/695
[58] Field of Search .................................. 568/673, 675, 568/687, 693, 695

[56] References Cited

U.S. PATENT DOCUMENTS

| | | | |
|---|---|---|---|
| 4,533,761 | 8/1985 | Marvin ..................................... | 568/673 |
| 5,416,240 | 5/1995 | Weyer et al. ............................ | 568/617 |
| 5,714,638 | 2/1998 | Weyer et al. ............................ | 568/617 |

OTHER PUBLICATIONS

Caplus 91:210821; J. Chem. Soc. Chem Commun.; pp. 330–331, 1979, vol. 7, Jul. 1979.

*Primary Examiner*—Alan L. Rotman
*Assistant Examiner*—Rita Desai
*Attorney, Agent, or Firm*—Keil & Weinkauf

[57] ABSTRACT

A process for preparing tetrahydrofuran, which comprises reacting 1,4-butenediol diethers of the formulae I and/or II

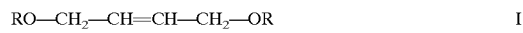
$$RO-CH_2-CH=CH-CH_2-OR \qquad\qquad I$$

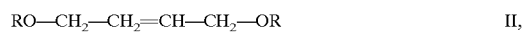

$$RO-CH_2-CH_2=CH-CH_2-OR \qquad\qquad II,$$

where the R radicals can be identical or different and are $C_1$–$C_{15}$-alkyl or cycloalkyl radicals, $C_6$–$C_{12}$-aryl radicals or $C_7$–$C_{15}$-aralkyl radicals, with water and hydrogen at from 20 to 300° C. under from 1 to 300 bar in the presence of catalysts or catalyst combinations which comprise components which are both capable of hydrogenation and have acidic or basic centers and a novel process for preparing 1,4-butanediol diethers of the formula I by metathesis are described.

The invention furthermore relates to the separate preparation of 1,4-butanediol monoethers of the formula III

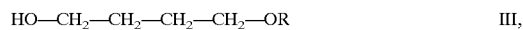
$$HO-CH_2-CH_2-CH_2-CH_2-OR \qquad\qquad III,$$

where R has the meanings indicated for formulae I and II, for which purpose 1,4-butanediol diethers of the formulae I and/or II are reacted as claimed in claim 1 with water and hydrogen in the presence of a hydrogenation catalyst at from 20 to 300° C. under from 1 to 300 bar.

9 Claims, No Drawings

PROCESS FOR THE PREPARATION OF 1,4-BUTANEDIOL MONOETHERS

CROSS REFERENCE TO RELATED APPLICATIONS

The present application is a Divisional Application of application Ser. No. 09/180,482, filed on Nov. 12, 1998, which is pending.

TECHNICAL FIELD

The present invention relates to a process for preparing tetrahydrofuran by reacting dialkoxybutenes with water and hydrogen in the presence of catalysts or catalyst combinations which are both capable of hydrogenation and have acidic or basic centers.

BACKGROUND ART

Tetrahydrofuran is obtained industrially on a large scale by cyclization of 1,4-butanediol (Weissermel, Arpe Industrielle Organische Chem., 4th Edition, VCH Verlagsgesellschaft Weinheim, 1994, page 111). Another possibility for preparing it comprises hydrogenation of dihydrofuran (EP-A 524 216).

The starting materials for the precursors in these cases are acetylene, propylene or propylene oxide, maleic anhydride or butadiene. Because butadiene is very readily available, there is now a preferential search for novel processes starting from butadiene and allowing tetrahydrofuran to be prepared in a simpler manner and at lower cost, the intention being in particular to reduce the number of reaction stages.

Intermediates based on the starting material butadiene are dialkoxybutenes which may be in the form of 1,4-dialkoxy-2-butenes (in cis and trans forms) and of 1,4-dialkoxy-1-butenes.

They can be described by the general formulae

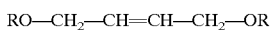

and

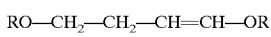

where R is identical or different $C_1$–$C_{15}$-alkyl or cycloalkyl, $C_6$–$C_{12}$-aryl or $C_7$–$C_{15}$-aralkyl radicals.

The 1,4-butenediol diethers of the formulae I and II can be prepared in various ways, eg. by reacting dibromobutene with two equivalents of alcohols, by oxidative additions of alcohols onto butadiene (SU-A 1 046 238 or EP-A 462 031) or by addition of alcohols onto vinyloxirane (WO-A 8 902 883).

Another method, to which this invention likewise relates, comprises addition of alcohols onto butadiene to form monoalkoxybutenes as disclosed in WO 95/19334 and metathesis thereof to dialkoxy-2-butenes and 2-butene.

DISCLOSURE OF INVENTION

We have found that tetrahydrofuran can be prepared in good yield in a few stages starting from butadiene when 1,4-butenediol diethers of the formulae I and/or II

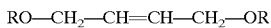

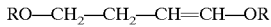

where the R radicals can be identical or different and are $C_1$–$C_{15}$-alkyl or cycloalkyl radicals, $C_6$–$C_{12}$-aryl radicals or $C_7$–$C_{15}$-aralkyl radicals, are reacted with water and hydrogen at from 20 to 300° C. under from 1 to 300 bar in the presence of catalysts or catalyst combinations which comprise components which are both capable of hydrogenation and have acidic or basic centers.

It is assumed that the reaction according to the invention takes place by the individual steps depicted in the following scheme:

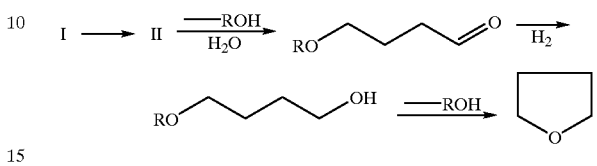

it being possible to return the eliminated alcohol to the preparation of the starting compounds I and II.

The following information is available in the literature on the individual steps assumed for this:

Isomerization of dialkoxy-2-butenes to the corresponding di-alkoxy-1-butenes has not been described. However, the isomerization of bistrimethylsilyl 2-butene ether to bistrimethylsilyl 1-butene ether (C. Malanga et al. Tetrahedron Lett. 36 (1995) 1133–1136) with nickel hydrides is to be regarded as similar.

Nor is the hydrolytic cleavage of dialkoxy-1-butenes to the corresponding alcohol and aldehyde ether known, the literature containing only examples of the acid-catalyzed hydrolysis of simple enol ethers (eg. T. Okuyama et al., J. Am. Chem. Soc. 89 (1967) 5826–5831).

Hydrogenation of aldehyde ethers with Raney nickel as catalyst (compounds alkylated in the alpha position are exclusively used as alkoxy radical) to the corresponding 4-alkoxybutanols is described, as is the subsequent cyclization to THF on acidic catalysts, in EP 18 164 B1. However, in this case the ether component is eliminated not only as alcohol but also as the corresponding dehydrated product, ie. as olefin, which can be reused only with difficulty in a cyclic process which is preferred for economic reasons. If the olefin is produced, in addition THF is not the primary product, but 1,4-butanediol is and forms THF only after elimination of water.

In the light of the abovementioned prior art, it was surprising that it is possible to obtain THF from dialkoxybutenes of the formulae I and II in one or a maximum of two stages and, at the same time, to obtain the alcohol component (hence with the possibility of recycling and design of a cyclic process) with high selectivity.

The reaction can take place in one or two stages.

In the one-stage variant, the compounds of the formulae I and/or II are reacted in the gas or liquid phase in the presence of water and hydrogen, and of a catalyst which is capable of hydrogenation and which has either Brönsted and/or Lewis acid or base centers, or to which an appropriate catalyst which is a Brönsted and/or Lewis acid or base has been added, to give THF and alcohol.

The R radicals in the precursor and intermediates may be different but are preferably the same. The radicals preferably used are those which afford a primary alcohol after elimination.

In the two-stage variant, compounds of the formulae I and/or II are reacted in the presence of water and hydrogen and of a hydrogenation catalyst to give 1,4-butanediol monoether which is then, with or without intermediate purification, converted on an acidic or basic catalyst into THF and alcohol.

The one- or two-stage process can be carried out batchwise or, preferably, continuously.

The description of the following features of the process applies both to the one-stage procedure and to the first stage of the two-stage variant:

The molar ratio of water to 1,4-butenediol diethers of the formulae I and/or II is 100:1, preferably 50:1, particularly preferably 10:1.

The reaction pressure, which is essentially determined by hydrogen, is from 1 to 300 bar, preferably 1 to 200 bar, particularly preferably 1 to 100 bar, and the reaction temperatures are in the range from 20 to 300° C., preferably 40 to 270° C., particularly preferably 80 to 200° C.

Catalysts particularly used according to the invention are those capable of catalytic hydrogenation of ketones or aldehydes with hydrogen to alcohols. As a rule, they contain one or more elements of subgroup I, II, VI–VIII or main group III–V of the periodic table of the elements or compounds thereof. The catalysts may be in the form of homogeneous solutions (examples in H. Kropf, Methoden der organischen Chemie (Houben-Weyl), Volume IV/1c, Georg Thieme Verlag Stuttgart, 1980, pages 45–67) or heterogeneous.

Examples of preferred homogeneous catalysts are complexes of rhodium, ruthenium, iridium, palladium, platinum and cobalts with phosphine or phosphite ligands, whose preparation is described, for example, in CA-A 7 276 41, H. Brunner in Hartley: The chemistry of the metal-carbon bond; Vol. 5, pages 110–124, John Wiley & Sons, New York 1989 and Tóth et al., Inorg. Chim. Acta 42, (1980) 153 and in the literature cited therein. Suitable metal complexes are furthermore described in WO 95-19 334.

Ru complexes are particularly preferred. Examples which may be mentioned are $HRuCl(CO)(TPP)_3$ and $H_2Ru(CO)(TPP)_3$ (TPP=triphenylphosphine).

The heterogeneous catalysts may be employed either in a fixed arrangement, or else mobile, eg. in a fluidized bed reactor, or in suspension. Examples thereof are described, for example, in Houben-Weyl, Methoden der Organischen Chemie, Volume IV/1c, pages 16 to 26.

Preferred among these hydrogenation catalysts are those containing one or more elements of group Ib, IIb, VIb, VIIb and VIII, in particular copper, chromium, rhenium, cobalt, rhodium, nickel, palladium, ruthenium, iron and platinum or compounds thereof.

The catalysts employed in the process according to the invention may be, for example, what are called precipitated catalysts. Catalysts of this type can be prepared by precipitating their catalytically active components from solutions of their salts, in particular from solutions of their nitrates and/or acetates, for example by adding solutions of alkali metal and/or alkaline earth metal hydroxides and/or carbonates, eg. as sparingly soluble hydroxides, oxide hydrates, basic salts or carbonates, subsequently drying the precipitates and then converting them by calcination at, in general, 300 to 700° C., in particular 400 to 600° C., into the corresponding oxides, mixed oxides and/or mixed valency oxides, which are reduced by treatment with hydrogen or with hydrogen-containing gases at, as a rule, 50 to 700° C., in particular 100 to 400° C., into the relevant metals and/or oxidic compounds in a low oxidation state and converted into the actual catalytically active form. This reduction is, as a rule, continued until water is no longer formed. In the preparation of precipitated catalysts containing a carrier material, the precipitation of the catalytically active components can take place in the presence of the relevant carrier material. The catalytically active components may, however, also advantageously be precipitated at the same time as the carrier material out of the relevant salt solution. The hydrogenation catalysts preferably employed in the process according to the invention are those containing the metals or metal compounds catalyzing the hydrogenation deposited on a carrier material. Apart from the abovementioned precipitated catalysts which, apart from the catalytically active components, additionally contain a carrier material, also suitable for the process according to the invention are in general those carrier materials in which the components with catalytic hydrogenation activity have been applied to a carrier material, eg. by impregnation.

The manner of applying the catalytically active metals to the carrier is, as a rule, not critical and can be brought about in a variety of ways. The catalytically active metals can be applied to these carrier materials for example by impregnation with solutions or suspensions of the salts or oxides of the relevant elements, drying and subsequently reducing the metal compounds to the relevant metals or compounds of low oxidation state using a reducing agent, preferably with hydrogen or complex hydrides. Another possibility for applying the catalytically active metals to these carriers comprises impregnating the carriers with solutions of salts which readily undergo thermal decomposition, eg. with nitrates or complex compounds which readily undergo thermal decomposition, eg, carbonyl or hydrido complexes of the catalytically active metals, and heating the impregnated carrier at from 300 to 600° C. in order thermally to decompose the adsorbed metal compounds. This thermal decomposition is preferably carried out under a protective gas atmosphere. Examples of suitable protective gases are nitrogen, carbon dioxide, hydrogen or the inert gases.

The catalytically active metals can also be deposited on the catalyst carrier by vapor deposition or by flame spraying. The content of catalytically active metals in these supported catalysts is not in principle crucial for the success of the process according to the invention. It is self-evident to the skilled worker that higher space-time conversions may be achieved with higher contents of catalytically active metals in these supported catalysts than with lower contents. In general, the supported catalysts used contain from 0.1 to 90% by weight, preferably 0.5 to 40% by weight, of catalytically active metals based on the complete catalyst. Since these stated contents are based on the complete catalyst, including the carrier material, but different carrier materials may have very different specific gravities and specific surface areas, contents below or above these are also possible without this having a disadvantageous effect on the result of the process according to the invention. It is, of course, also possible to apply a plurality of catalytically active metals to the particular carrier material. It is furthermore possible for the catalytically active metals to be applied to the carrier, for example, by the process of DE-A 2 519 817, EP-A 1 477 219 and EP-A 285 420. In the catalysts disclosed in these publications, the catalytically active metals are present as alloys produced by thermal treatment and/or reduction of the, for example, by impregnation with a salt or complex of the abovementioned metals.

Activation both of the precipitated catalysts and of the support catalysts can also take place in situ at the start of the reaction by the hydrogen which is present, but these catalysts are preferably activated separately before use thereof.

It is possible to use as carrier materials in general the oxides of aluminum and titanium zirconium dioxide, silicon dioxide, aluminas, eg. montmorillonite, silicates such as magnesium or aluminum silicates, zeolites such as ZSM-5 or ZSM-10 zeolites, and active carbon. Preferred carrier materials are aluminum oxides, titanium dioxides, silicon dioxide, zirconium dioxide and active carbon. It is, of course, also possible to use mixtures of different carrier materials as carriers for catalysts which can be used in the process according to the invention.

Examples which may be mentioned of heterogeneous catalysts which can be employed in the process according to the invention are the following:

Platinum on active carbon, palladium on active carbon, palladium on aluminum oxide, cobalt on active carbon, cobalt on silicon dioxide, cobalt on aluminum oxide, iron on active carbon, manganese on active carbon, rhenium on active carbon, rhenium on silicon dioxide, rhenium/tin on active carbon, rhenium/palladium on active carbon, copper on active carbon, copper on silicon dioxide, copper on aluminum oxide, copper chromite, barium copper chromite, and the catalysts disclosed in DE-A 3 932 332, U.S. Pat. No. 3,449,445, EP-A 44 444, EP-A 147 219, DE-A 3 904 083, DE-A 2 321 101, WEP-A 415 202, DE-A 2 366 264 and EP-A 100 406.

Particularly preferred catalysts contain at least one of the metals copper, ruthenium or rhenium.

Brönsted and/or Lewis acids or bases can be applied to the catalyst for a gas-phase reaction, but can also be in the form of a homogeneous solution for liquid-phase reactions. Brönsted and/or Lewis acids are preferred. Acids or bases which are preferably employed are listed below.

If the reaction is carried out in two stages, the discharge from the first stage can, where appropriate after removal of the catalyst, be separated either directly or advantageously by distillation into the components of alcohol, where appropriate excess water, and 4-alkoxybutanol, the latter being reused for liberation of THF, in either the gas or liquid phase.

Cyclization to THF and alcohol can be carried out on basic or, preferably, acidic, homogeneous or heterogeneous catalysts.

Examples of basic catalysts are alkali metal or alkaline earth metal oxides or hydroxides or carrier materials which contain these alkaline components, eg. impregnated or sprayed on, or basic ion exchangers.

Examples of acidic catalysts are zeolites in the H form, acidic ion exchangers, heteropolyacids, acidic and superacidic metal oxides, which have, where appropriate, been doped with sulfate or phosphate, and inorganic or organic acids.

Examples of suitable zeolites are representatives of the mordenite group or narrow-pore zeolites of the erionite or chabasite type or zeolites of the faujasite type, eg. Y, X or L zeolites. This group also includes the "ultrastable" zeolites of the faujasite type, ie. dealuminated zeolites.

Particularly advantageous zeolites are those with a pentasil structure such as ZSM-5, ZSM-11 and ZBM-10. These have a common basic building block in the form of five-membered ring composed of $SiO_2$ tetrahedra. They have a high $SiO_2/Al_2O_3$ ratio and pore sizes which are between those of zeolites of type A and those of type X or Y.

Equally suitable acidic catalysts are heteropolyacids, eg. inorganic polyacids which, in contrast to isopolyacids, have at least two different central atoms. Examples which may be mentioned are phosphotungstic acid $H_3PW_{12}O_{40}\cdot xH_2O$ and phosphomolybdic acid $H_3PMo_{12}O_{40}\cdot xH_2O$. It is possible in principle for the catalysts and catalyst combinations mentioned in EP-A 158 229 to be employed.

Preferred heteropolyacids are heteropolyacids of molybdenum or tungsten with phosphoric acid, telluric acid, selenic acid, arsenic acid, silicic acid, in particular with phosphoric acid.

The protons of the heteropolyacids may be partly replaced by metal ions, and in this case alkali metal and alkaline earth metal ions are preferred.

Also suitable are acidic ion exchangers, eg. crosslinked polystyrenes with sulfo groups, or acidic metal oxides, for example $SiO_2$, $Al_2O_3$, $ZrO_2$, $TiO_2$, $SnO_2$, $TiO_2$, etc., or combinations of individual oxides. The oxides can also be treated with mineral acids such as sulfuric acid to increase the acid strength.

Also suitable as acids are mineral acids such as sulfuric acid and phosphoric acid, and organic acids such as sulfonic acids.

If the reaction is carried out in two stages, the temperature in the second stage of the reaction according to the invention is maintained at from 30 to 300° C., preferably 40 to 280° C., particularly preferably 60 to 250° C.

The pressure in the reaction may, depending on the system chosen, be slightly reduced or slightly elevated. It is in general from 0.1 to 10 bar, preferably 0.5 to 5 bar, particularly preferably 0.8 to 4 bar.

The reaction products can be removed by a stream of inert gas, preferably from homogeneous reaction mixtures.

The reaction products—THF and alcohol—are separated in a conventional manner, preferably by distillation.

Another possible way of carrying out the process according to the invention is a combination of one- and two-stage variants. In this case it is possible for the 4-alkoxybutanol which has not been completely converted into THF and alcohol under the conditions of the one-stage process to be converted completely under the conditions according to the invention in the second stage.

The invention furthermore relates to the separate preparation of 1,4-butanediol monoethers of the formula III

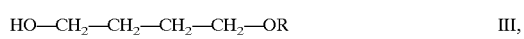

where R has the meanings indicated for formulae I and II, for which purpose 1,4-butanediol diethers of the formulae I and/or II are reacted as claimed in claim 1 with water and hydrogen in the presence of a hydrogenation catalyst at from 20 to 300° C. under from 1 to 300 bar.

Suitable hydrogenation catalysts are all the abovementioned catalysts which catalyze the further reaction to tetrahydrofuran, but without acidic or basic centers. The butanediol monoethers of the formula III are valuable intermediates and are used as $C_4$ building blocks in the synthesis of active substances and plastics.

The invention furthermore relates to a novel preparation of the starting materials of the formula I by metathesis, where 2-butenol ethers of the formula IV

where R has the meanings stated for formulae I and II, are converted in the presence of a metathesis catalyst into butene and 1,4-butenediol diethers of the formula I

where R has the meanings mentioned for formula I hereinbefore, with the proviso that the two Rs have the same meaning.

The reaction takes place as shown in the following scheme, with 1,4-dialkoxybutenes being formed from 1-alkoxybutenes with elimination of 2-butene in the presence of a catalyst

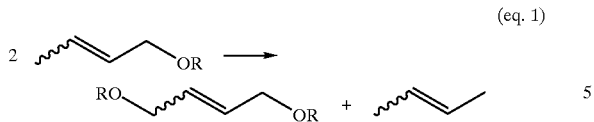

(eq. 1)

Metathesis catalysts to be used according to the invention are those capable of olefin metathesis as shown in eq. 2.

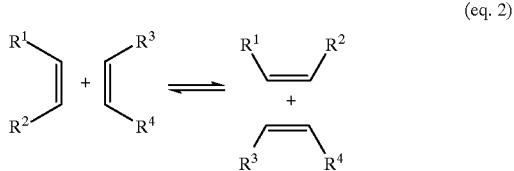

(eq. 2)

Suitable metathesis catalysts are homogeneous and heterogeneous compounds of the transition metals, in particular of subgroup IV, VI, VII and VIII of the periodic table of the elements, and homogeneous and heterogeneous catalyst systems containing these compounds. Examples of such catalysts are described in the literature (eg. G. W. Parshall, S. D. Ittel, Homogeneous Catalysis, 2nd Edition, 1992, Wiley, pages 217 et seq.; R. L. Banks, Catalysis, Vol. pages 100 et seq.; R. H. Grubbs, Progress in Inorg. Chem., Vol. 24, pages 1 et seq.).

Preferred catalysts are ruthenium compounds of the general composition $RuX_2(=CHR)(PR'_3)_2$ as described by Grubbs in WO 93/20111, where X is halogen, R is hydrogen, alkyl or aryl and R' is alkyl. Also suitable and preferred are mixtures of compounds of the formula $[Ru(\eta^6\text{-arene})X_2]_2/(PR_3)/N_2CHR'$, whose suitability as metathesis catalyst is described by Noels in J. Chem. Soc., Chem. Commun.; 1995, 1127 et seq., where arene is, for example, benzene, mesitylene or cymene, X is halogen, R is alkyl and R' is hydrogen, alkyl, aryl or trimethylsilyl.

MODE(S) FOR CARRYING OUT THE INVENTION

The complex $RuCl_2(=CHPh)(PCy_3)_2$ (Cy=cyclohexyl), and a catalyst system based on the commercially available compounds $[Ru(\eta^6\text{-p-cymene})Cl_2]_2/PCy_3/N_2CHSiMe_3$ are particularly preferred. In place of the components $Ru(\eta^6\text{-p-cymene})Cl_2$ and $PCy_3$, it is also possible to employ the product of their reaction, the complex $[Ru(\eta^6\text{-p-cymene})(PCy_3)Cl_2]$.

U.S. Pat. No. 5,342,985 (DE 39 40 196 A) and J. Chem. Soc., Chem. Commun. (1979) 330–331 describe the synthesis of 1,4-dialkoxybutenes from the corresponding allyl ethers with elimination of ethylene in the presence of heterogeneous Re compounds as metathesis catalysts.

However, it is known from the literature that transition metal compounds, especially those of ruthenium, are able to isomerize unsaturated ethers such as allyl and butenyl ethers as shown in eq. 3. An ether cleavage then takes place in the presence of water, resulting in the corresponding aldehydes.

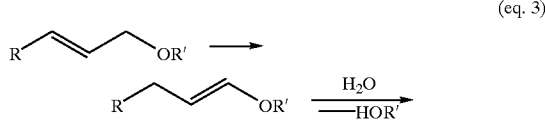

(eq. 3)

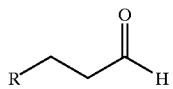

It was therefore surprising that the 1-alkoxy-2-butenes which are, in principle, less susceptible to metathesis reactions (by comparison with the allyl ethers) do not in the presence of Ru compounds isomerize to the 1-alkoxy-1-butenes but, on the contrary, selectively form 1,4-dialkoxybutenes with elimination of 2-butene.

Since the metathesis reaction is an alternative which is favorable industrially and, compared with the use of dibromobutenes, environmentally, it is preferred to use the butenediol diethers prepared by metathesis as precursors for the tetrahydrofuran preparation according to the invention.

The process according to the invention is explained in detail, but in no way restricted, by the following examples. The analysis took place by gas chromatography. The dibutoxybutene employed in the examples had a purity of about 98%.

EXAMPLE 1

200 ml of a copper/active carbon catalyst (Cu content calculated as CuO about 10% on 4 mm active carbon pellets; copper applied as ammoniate) were packed into a 200 ml tubular reactor and activated in a stream of hydrogen at about 180° C. Then, through two feeds, a 10% by weight solution of dibutoxy-2-butene in n-butanol (11 g/h) and 11 g of water/h, each gaseous, were passed in the stream of hydrogen (40 l/h) under 1 bar and at 230° C. over the catalyst zone. The discharge from the reaction was in two phases. Samples were taken at hourly intervals and analyzed by gas chromatography. The organic phase contained (calculated anhydrous) from 95 to 98% n-butanol and about 0.8% THF. The aqueous phase contained (calculated anhydrous) 95% n-butanol and about 0.5% THF.

EXAMPLE 2

200 ml of a rhenium/active carbon catalyst (Re content about 6% by weight on 4 mm active carbon pellets, Re applied as $Re_2O_7$) were activated at 300° C. as in Example 1. Then about 12 g/h dibutoxy-2-butene and about 11 g of water/h were passed with an $H_2$ carrier gas stream of 25 l/h over the catalyst at 220° C. The discharge contained 59% butanol and 30% THF.

EXAMPLE 3: (two-stage preparation)

a) 5 g of dibutoxy-2-butene, 5 g of water, 0.1 g of HRuCl(CO)(TPP)$_3$ and 0.05 g of TPP (triphenylphosphine) were introduced into a 72 ml metal autoclave and 50 bar of hydrogen were injected. The autoclave was then heated to 150° C. with stirring and, after 2 hours, cooled. The remaining pressure amounted to 40 bar. The two-phase discharge from the reaction was homogenized with 13 g of methanol for analytical purposes. About 80% 4-butoxybutanol and about 17% butanol were found.

b) 10 g of powdered $Al_2O_3$ and 18 g of 4-butoxybutanol were introduced into the bottom of a distillation apparatus and heated to 175° C. The reaction products distilled out at this temperature. Fresh 4-butoxybutanol was used for continuous replenishment at the rate the products distilled out. The distillate contained about 3% precursor, 52% butanol and 45% THF.

EXAMPLE 4: (Preparation of dialkoxybutene by metathesis)

41 mg of $RuCl_2(=CHPh)(PCy_3)_2$ (Cy=cyclohexyl) were mixed with 8.0 g of 1-butoxy-2-butene under an argon atmosphere in a glass vessel, and the mixture was stirred at room temperature. The butene produced in the reaction was able to escape through a bubble counter. After 12 h, the reaction mixture was analyzed by gas chromatography (coupled GC/MS). Besides the starting compound 1-butoxy-2-butene (51.6 and 18.6% area, E and Z isomers) and dibutyl ether (4.2% area), 1,4-dibutoxy-2-butene (4.78 and 17.1% area, E and Z isomers) and 2-butene (2.9% area) were detected. 1,4-Dibutoxy-1-butene (0.7% area) was identified as subsidiary component.

EXAMPLE 5

The procedure was as described in Example 4 but using $[Ru(\eta^6\text{-p-cymene})(PCy_3)Cl_2]/N_2CHSiMe_3$ as catalyst. After 12 h at 60° C., 1,4-dibutoxybutene (1.9 and 3.0% area) is detected by gas chromatography.

We claim:

1. A process for preparing 1,4-butanediol monoethers of the formula III

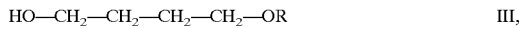

HO—CH$_2$—CH$_2$—CH$_2$—CH$_2$—OR          III, where R is a $C_1$–$C_{15}$-alkyl or cycloalkyl radical, a $C_6$–$C_{12}$-aryl radical or a $C_7$–$C_{15}$-aralkyl radical, which comprises reacting 1,4-butanediol diethers of the formulae I and/or II

RO—CH$_2$—CH=CH—CH$_2$—OR          I

RO—CH$_2$—CH$_2$—CH=CH—OR          II, where the R radicals can be identical or different, with water and hydrogen in the presence of a hydrogenation catalyst at from 20 to 300° C. under from 1 to 300 bar.

2. The process defined in claim 1, wherein the hydrogenation catalyst comprises one or more of the elements rhenium, copper or ruthenium or their compounds.

3. The process defined in claim 1, which is carried out in the gas phase or the liquid phase.

4. The process defined in claim 1, which is carried out continuously.

5. The process defined in claim 1, wherein water is present in an amount of 100 mol, per mol of the 1,4-butenediol diesters of the formula I and/or II, or less.

6. The process defined in claim 1, wherein the catalyst is employed in the form of homogeneous solutions.

7. The process defined in claim 1, wherein the catalyst comprises one or more of the following elements or compounds thereof: copper, chromium, rhenium, cobalt, rhodium, nickel, palladium, ruthenium, iron and platinum.

8. The process defined in claim 1, wherein the catalyst is employed in the form of a catalyst supported by a carrier material, wherein the catalytically active components are applied to the carrier material by way of precipitation, impregnation, by vapor deposition or by flame spraying.

9. The process defined in claim 8, wherein the catalyst comprises one or more of the following: platinum on active carbon, palladium on active carbon, palladium on aluminum oxide, cobalt on active carbon, cobalt on silicon dioxide, cobalt on aluminium oxide, iron on active carbon, manganese on active carbon, rhenium on acetic carbon, rhenium on silicon dioxide, rhenium/tin on active carbon, rhenium/palladium on active carbon, copper on active carbon, copper on silicon dioxide, copper on aluminum oxide, copper chromite and barium copper chromite.

* * * * *